United States Patent
Hess et al.

(10) Patent No.: US 8,475,490 B2
(45) Date of Patent: Jul. 2, 2013

(54) METHODS AND DEVICES FOR PROVIDING ACCESS THROUGH TISSUE TO A SURGICAL SITE

(75) Inventors: Christopher J. Hess, Cincinnati, OH (US); Daniel H. Duke, West Chester, OH (US); Daniel J. Mumaw, Cincinnati, OH (US); Katherine J. Schmid, Cincinnati, OH (US); Christopher W. Widenhouse, Clarksville, OH (US); Frederick E. Shelton, IV, Hillsboro, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 805 days.

(21) Appl. No.: 12/479,293

(22) Filed: Jun. 5, 2009

(65) Prior Publication Data
US 2010/0312061 A1    Dec. 9, 2010

(51) Int. Cl.
*A61B 17/02* (2006.01)
(52) U.S. Cl.
USPC .......................................... 606/201; 606/206
(58) Field of Classification Search
USPC .................... 600/184–200, 201–219
See application file for complete search history.

(56) References Cited

U.S. PATENT DOCUMENTS

| | | | |
|---|---|---|---|
| 2,129,391 A | 9/1938 | Wappler | |
| 3,402,710 A | 9/1968 | Paleschuck | |
| 3,654,965 A | 4/1972 | Gramain | |
| 4,112,932 A | 9/1978 | Chiulli | |
| 4,306,545 A | 12/1981 | Ivan et al. | |
| 4,379,458 A | 4/1983 | Bauer et al. | |
| 4,402,683 A | 9/1983 | Kopman | |
| 4,417,888 A | 11/1983 | Cosentino et al. | |
| 4,481,001 A * | 11/1984 | Graham et al. | 434/267 |
| 5,010,925 A | 4/1991 | Atkinson et al. | |
| 5,091,435 A | 2/1992 | Suzuki et al. | |

(Continued)

FOREIGN PATENT DOCUMENTS

| | | |
|---|---|---|
| DE | 19814576 A1 | 10/1999 |
| DE | 20022005 U1 | 4/2001 |

(Continued)

OTHER PUBLICATIONS

"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport > R-Port laparoscopic access device > Advanced Surgical Concepts ASC" Ideas for Surgery.com, Dec. 2007, 4 pages.

(Continued)

*Primary Examiner* — Jerry Cumberledge

(57) ABSTRACT

Methods and devices are provided for providing access through tissue to a surgical site. A surgical access device can be configured to be positioned in tissue to provide access through a working channel of the access device to a body cavity underlying the tissue. The access device can include a sealing element positioned at least partially within the working channel. The sealing element can be formed of a puncturable self-sealing material such as a gel and/or a foam configured to provide a channel seal that seals the working channel when no instrument is inserted through the sealing element and configured to provide an instrument seal that provides a seal around one or more surgical instruments inserted through the sealing element.

16 Claims, 6 Drawing Sheets

U.S. PATENT DOCUMENTS

| | | | |
|---|---|---|---|
| 5,183,471 A | 2/1993 | Wilk | |
| 5,197,955 A | 3/1993 | Stephens et al. | |
| 5,207,213 A | 5/1993 | Auhll et al. | |
| 5,209,737 A | 5/1993 | Ritchart et al. | |
| 5,209,741 A | 5/1993 | Spaeth | |
| 5,235,966 A | 8/1993 | Jamner | |
| 5,269,772 A | 12/1993 | Wilk | |
| 5,308,336 A | 5/1994 | Hart et al. | |
| 5,312,417 A | 5/1994 | Wilk | |
| 5,320,611 A | 6/1994 | Bonutti et al. | |
| 5,342,315 A | 8/1994 | Rowe et al. | |
| 5,366,478 A | 11/1994 | Brinkerhoff et al. | |
| 5,385,553 A | 1/1995 | Hart et al. | |
| 5,385,560 A | 1/1995 | Wulf | |
| 5,391,154 A | 2/1995 | Young | |
| 5,431,676 A | 7/1995 | Dubrul et al. | |
| 5,443,452 A | 8/1995 | Hart et al. | |
| 5,443,484 A | 8/1995 | Kirsch et al. | |
| 5,476,475 A | 12/1995 | Gadberry | |
| 5,480,410 A | 1/1996 | Cuschieri et al. | |
| 5,531,758 A | 7/1996 | Uschold et al. | |
| 5,545,179 A | 8/1996 | Williamson, IV | |
| 5,562,677 A | 10/1996 | Hildwein et al. | |
| 5,569,205 A | 10/1996 | Hart et al. | |
| 5,569,254 A | 10/1996 | Carlson et al. | |
| 5,584,850 A | 12/1996 | Hart et al. | |
| 5,628,732 A | 5/1997 | Antoon, Jr. et al. | |
| 5,634,911 A | 6/1997 | Hermann et al. | |
| 5,634,937 A | 6/1997 | Mollenauer et al. | |
| 5,643,301 A | 7/1997 | Mollenauer | |
| 5,653,705 A | 8/1997 | de la Torre et al. | |
| 5,653,718 A | 8/1997 | Yoon | |
| 5,672,168 A | 9/1997 | de la Torre et al. | |
| 5,676,657 A | 10/1997 | Yoon | |
| 5,695,448 A | 12/1997 | Kimura et al. | |
| 5,707,359 A | 1/1998 | Bufalini | |
| 5,752,970 A | 5/1998 | Yoon | |
| 5,782,812 A | 7/1998 | Hart et al. | |
| 5,797,888 A | 8/1998 | Yoon | |
| 5,803,919 A | 9/1998 | Hart et al. | |
| 5,814,058 A | 9/1998 | Carlson et al. | |
| 5,827,319 A | 10/1998 | Carlson et al. | |
| 5,843,040 A | 12/1998 | Exline | |
| 5,865,807 A | 2/1999 | Blake, III | |
| 5,868,762 A | 2/1999 | Cragg et al. | |
| 5,882,344 A | 3/1999 | Stouder, Jr. | |
| 5,891,013 A | 4/1999 | Thompson | |
| 5,899,208 A | 5/1999 | Bonadio | |
| 5,906,577 A | 5/1999 | Beane et al. | |
| 5,946,280 A | 8/1999 | Ohkubo | |
| 5,957,913 A | 9/1999 | de la Torre et al. | |
| 5,990,382 A | 11/1999 | Fox | |
| 5,997,515 A | 12/1999 | de la Torre et al. | |
| 6,024,736 A | 2/2000 | de la Torre et al. | |
| RE36,702 E | 5/2000 | Green et al. | |
| 6,056,766 A | 5/2000 | Thompson et al. | |
| 6,066,090 A | 5/2000 | Yoon | |
| 6,077,288 A | 6/2000 | Shimomura et al. | |
| 6,080,174 A | 6/2000 | Dubrul et al. | |
| 6,086,603 A | 7/2000 | Termin et al. | |
| 6,120,513 A | 9/2000 | Bailey et al. | |
| 6,123,689 A | 9/2000 | To et al. | |
| 6,142,396 A | 11/2000 | Gallus | |
| 6,142,936 A | 11/2000 | Beane et al. | |
| 6,162,196 A | 12/2000 | Hart et al. | |
| 6,217,555 B1 | 4/2001 | Hart et al. | |
| 6,245,052 B1 | 6/2001 | Orth et al. | |
| 6,258,069 B1 | 7/2001 | Carpentier et al. | |
| 6,277,064 B1 | 8/2001 | Yoon | |
| 6,315,770 B1 | 11/2001 | de la Torre et al. | |
| 6,319,246 B1 | 11/2001 | de la Torre et al. | |
| 6,325,812 B1 | 12/2001 | Dubrul et al. | |
| 6,348,034 B1 | 2/2002 | Thompson | |
| 6,352,503 B1 | 3/2002 | Matsui et al. | |
| 6,440,061 B1 | 8/2002 | Wenner et al. | |
| 6,440,063 B1 | 8/2002 | Beane et al. | |
| 6,447,489 B1 | 9/2002 | Peterson | |
| 6,454,783 B1 | 9/2002 | Piskun | |
| 6,458,077 B1 | 10/2002 | Boebel et al. | |
| 6,488,620 B1 | 12/2002 | Segermark et al. | |
| 6,551,270 B1 | 4/2003 | Bimbo et al. | |
| 6,551,282 B1 | 4/2003 | Exline et al. | |
| 6,589,167 B1 | 7/2003 | Shimomura et al. | |
| 6,605,063 B2 | 8/2003 | Bousquet | |
| 6,669,674 B1 | 12/2003 | Macoviak et al. | |
| 6,702,787 B2 | 3/2004 | Racenet et al. | |
| 6,706,033 B1 | 3/2004 | Martinez et al. | |
| 6,706,050 B1 | 3/2004 | Giannadakis | |
| 6,908,430 B2 | 6/2005 | Caldwell et al. | |
| 6,939,296 B2 | 9/2005 | Ewers et al. | |
| 6,945,932 B1 | 9/2005 | Caldwell et al. | |
| 6,972,026 B1 | 12/2005 | Caldwell et al. | |
| 7,014,628 B2 | 3/2006 | Bousquet | |
| 7,052,454 B2 | 5/2006 | Taylor | |
| 7,083,626 B2 | 8/2006 | Hart et al. | |
| 7,118,528 B1 | 10/2006 | Piskun | |
| 7,154,017 B2* | 12/2006 | Sigurjonsson et al. | 602/41 |
| 7,163,510 B2 | 1/2007 | Kahle et al. | |
| 7,163,525 B2 | 1/2007 | Franer | |
| 7,214,185 B1 | 5/2007 | Rosney et al. | |
| 7,229,408 B2 | 6/2007 | Douglas et al. | |
| 7,338,473 B2 | 3/2008 | Campbell et al. | |
| 7,344,547 B2 | 3/2008 | Piskun | |
| 7,362,875 B2* | 4/2008 | Saxton et al. | 381/322 |
| 7,371,227 B2 | 5/2008 | Zeiner | |
| 7,393,322 B2 | 7/2008 | Wenchell | |
| 7,449,011 B2 | 11/2008 | Wenchell et al. | |
| 7,481,795 B2 | 1/2009 | Thompson et al. | |
| 8,105,234 B2* | 1/2012 | Ewers et al. | 600/208 |
| 2002/0156432 A1 | 10/2002 | Racenet et al. | |
| 2003/0028179 A1 | 2/2003 | Piskun | |
| 2003/0139756 A1 | 7/2003 | Brustad | |
| 2003/0216770 A1 | 11/2003 | Persidsky et al. | |
| 2004/0015185 A1 | 1/2004 | Ewers et al. | |
| 2004/0019322 A1 | 1/2004 | Hoffmann | |
| 2004/0082969 A1 | 4/2004 | Kerr | |
| 2004/0106942 A1 | 6/2004 | Taylor et al. | |
| 2004/0117032 A1 | 6/2004 | Roth | |
| 2004/0138528 A1 | 7/2004 | Richter et al. | |
| 2004/0199121 A1 | 10/2004 | Wenchell et al. | |
| 2004/0215063 A1 | 10/2004 | Bonadio et al. | |
| 2004/0230160 A1 | 11/2004 | Blanco | |
| 2004/0230161 A1 | 11/2004 | Zeiner | |
| 2004/0254426 A1 | 12/2004 | Wenchell | |
| 2004/0258263 A1* | 12/2004 | Saxton et al. | 381/328 |
| 2005/0020884 A1 | 1/2005 | Hart et al. | |
| 2005/0033342 A1 | 2/2005 | Hart et al. | |
| 2005/0085842 A1 | 4/2005 | Eversull et al. | |
| 2005/0137609 A1 | 6/2005 | Guiraudon | |
| 2005/0148823 A1 | 7/2005 | Vaugh et al. | |
| 2005/0155611 A1 | 7/2005 | Vaugh et al. | |
| 2005/0192483 A1 | 9/2005 | Bonadio et al. | |
| 2005/0209608 A1 | 9/2005 | O'Heeron | |
| 2005/0215862 A1 | 9/2005 | Larson et al. | |
| 2005/0216028 A1 | 9/2005 | Hart et al. | |
| 2005/0222582 A1 | 10/2005 | Wenchell | |
| 2005/0267419 A1 | 12/2005 | Smith | |
| 2005/0273132 A1 | 12/2005 | Shluzas et al. | |
| 2005/0277946 A1 | 12/2005 | Greenhalgh | |
| 2006/0012965 A1 | 1/2006 | Beall et al. | |
| 2006/0019592 A1 | 1/2006 | Kupferberg et al. | |
| 2006/0019723 A1 | 1/2006 | Vorenkamp et al. | |
| 2006/0020241 A1 | 1/2006 | Piskun et al. | |
| 2006/0020281 A1 | 1/2006 | Smith | |
| 2006/0021061 A1 | 1/2006 | Cerri et al. | |
| 2006/0021891 A1 | 2/2006 | Franer et al. | |
| 2006/0025813 A1 | 2/2006 | Shelton et al. | |
| 2006/0030755 A1 | 2/2006 | Ewers et al. | |
| 2006/0071432 A1 | 4/2006 | Staudner | |
| 2006/0079823 A1* | 4/2006 | Utterberg et al. | 602/53 |
| 2006/0129165 A1 | 6/2006 | Edoga et al. | |
| 2006/0212061 A1 | 9/2006 | Wenchell | |
| 2006/0212062 A1 | 9/2006 | Farascioni | |
| 2006/0217665 A1 | 9/2006 | Prosek | |
| 2006/0224129 A1 | 10/2006 | Beasley et al. | |
| 2006/0224164 A1 | 10/2006 | Hart et al. | |
| 2006/0229501 A1 | 10/2006 | Jensen et al. | |

| | | |
|---|---|---|
| 2006/0241651 A1 | 10/2006 | Wilk |
| 2006/0241671 A1 | 10/2006 | Greenhalgh |
| 2006/0247498 A1 | 11/2006 | Bonadio et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088204 A1 | 4/2007 | Albrecht et al. |
| 2007/0088258 A1 | 4/2007 | Wenchell et al. |
| 2007/0088277 A1 | 4/2007 | McGinley et al. |
| 2007/0118021 A1 | 5/2007 | Pokorney |
| 2007/0118175 A1 | 5/2007 | Butler et al. |
| 2007/0123968 A1* | 5/2007 | Weinberg ..................... 623/1.1 |
| 2007/0151566 A1 | 7/2007 | Kahle et al. |
| 2007/0185387 A1* | 8/2007 | Albrecht et al. ............. 600/208 |
| 2007/0185453 A1 | 8/2007 | Michael et al. |
| 2007/0208312 A1 | 9/2007 | Norton et al. |
| 2007/0255219 A1 | 11/2007 | Vaugh et al. |
| 2008/0009797 A1 | 1/2008 | Stellon et al. |
| 2008/0025519 A1 | 1/2008 | Yu et al. |
| 2008/0027476 A1 | 1/2008 | Piskun |
| 2008/0051739 A1 | 2/2008 | McFarlane |
| 2008/0058728 A1 | 3/2008 | Soltz et al. |
| 2008/0065021 A1 | 3/2008 | Jenkins et al. |
| 2008/0086080 A1 | 4/2008 | Mastri et al. |
| 2008/0119821 A1 | 5/2008 | Agnihotri et al. |
| 2008/0132765 A1 | 6/2008 | Beckman et al. |
| 2008/0255519 A1 | 10/2008 | Piskun et al. |
| 2008/0281161 A1 | 11/2008 | Albrecht et al. |
| 2009/0005799 A1 | 1/2009 | Franer et al. |
| 2009/0082731 A1 | 3/2009 | Moreno |
| 2009/0118587 A1 | 5/2009 | Voegele et al. |
| 2009/0187079 A1 | 7/2009 | Albrecht et al. |
| 2009/0270685 A1 | 10/2009 | Moreno et al. |
| 2009/0270686 A1 | 10/2009 | Duke et al. |
| 2009/0270818 A1 | 10/2009 | Duke |
| 2010/0010310 A1 | 1/2010 | Weisenburgh, II et al. |
| 2010/0081863 A1 | 4/2010 | Hess et al. |
| 2010/0081864 A1 | 4/2010 | Hess et al. |
| 2010/0081871 A1 | 4/2010 | Widenhouse et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0249525 A1 | 9/2010 | Shelton, IV et al. |
| 2010/0261970 A1 | 10/2010 | Shelton, IV et al. |
| 2010/0261972 A1 | 10/2010 | Widenhouse et al. |
| 2010/0261974 A1 | 10/2010 | Shelton, IV et al. |
| 2010/0262080 A1 | 10/2010 | Shelton, IV et al. |
| 2010/0268162 A1 | 10/2010 | Shelton, IV et al. |
| 2010/0274093 A1 | 10/2010 | Shelton, IV |
| 2010/0280327 A1 | 11/2010 | Nobis et al. |
| 2010/0312060 A1 | 12/2010 | Widenhouse et al. |
| 2010/0312061 A1 | 12/2010 | Hess et al. |
| 2010/0312062 A1 | 12/2010 | Cropper et al. |
| 2010/0312063 A1 | 12/2010 | Hess et al. |
| 2010/0312064 A1 | 12/2010 | Weisenburgh, II et al. |
| 2010/0312065 A1 | 12/2010 | Shelton, IV et al. |
| 2010/0312066 A1 | 12/2010 | Cropper et al. |
| 2010/0312189 A1 | 12/2010 | Shelton, IV et al. |
| 2012/0190915 A1* | 7/2012 | Shalon et al. .................. 600/29 |

FOREIGN PATENT DOCUMENTS

| | | |
|---|---|---|
| EP | 0568383 | 11/1993 |
| EP | 568383 A1 | 11/1993 |
| EP | 577400 A1 | 1/1994 |
| EP | 0637431 A1 | 2/1995 |
| EP | 0646358 | 4/1995 |
| EP | 646358 A1 | 4/1995 |
| EP | 709918 | 5/1996 |
| EP | 0776231 A1 | 6/1997 |
| EP | 0776231 B1 | 6/1997 |
| EP | 950376 | 10/1999 |
| EP | 1219251 A1 | 7/2002 |
| EP | 1219251 A1 | 7/2002 |
| EP | 1219252 A1 | 7/2002 |
| EP | 1219252 A1 | 7/2002 |
| EP | 1219253 A1 | 7/2002 |
| EP | 1219253 A1 | 7/2002 |
| EP | 1350476 | 10/2003 |
| EP | 1702575 A2 | 9/2006 |
| EP | 1731105 A1 | 12/2006 |
| EP | 1731105 A1 | 12/2006 |
| EP | 1774918 A1 | 4/2007 |
| EP | 2119404 A1 | 11/2009 |
| FR | 2710270 | 3/1995 |
| FR | 2710270 A1 | 3/1995 |
| JP | 2006320750 | 11/2006 |
| WO | 9407552 A1 | 4/1994 |
| WO | 9602297 A1 | 2/1996 |
| WO | 9608897 A1 | 3/1996 |
| WO | 9636283 A1 | 11/1996 |
| WO | 9743958 A1 | 11/1997 |
| WO | 0032263 A1 | 6/2000 |
| WO | 0041759 A1 | 7/2000 |
| WO | 0108563 A2 | 2/2001 |
| WO | 0217800 A2 | 3/2002 |
| WO | 2004030515 A2 | 4/2004 |
| WO | 200500454 A1 | 1/2005 |
| WO | 2005002454 A1 | 1/2005 |
| WO | 2005087112 A1 | 9/2005 |
| WO | WO-2005087112 A1 | 9/2005 |
| WO | 2005094432 A2 | 10/2005 |
| WO | 2005097019 A2 | 10/2005 |
| WO | 2005097234 A2 | 10/2005 |
| WO | WO-2005094432 A2 | 10/2005 |
| WO | 2006057982 A2 | 6/2006 |
| WO | 2007008741 A1 | 1/2007 |
| WO | 2007119232 A2 | 10/2007 |
| WO | WO-2007119232 A2 | 10/2007 |
| WO | 2008024502 A2 | 2/2008 |
| WO | WO-2008024502 A2 | 2/2008 |
| WO | 2008028149 A2 | 3/2008 |
| WO | 2008121294 A1 | 10/2008 |
| WO | 2009035663 A2 | 3/2009 |

OTHER PUBLICATIONS

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp: 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

U.S. Appl. No. 12/399,482, filed Mar. 6, 2009.

U.S. Appl. No. 12/399,547, filed Mar. 6, 2009.
U.S. Appl. No. 12/399,625, filed Mar. 6, 2009.
U.S. Appl. No. 12/427,964, filed Apr. 22, 2009.
International Search Report and Written Opinion for International App. No. PCT/US2010/036811 dated Sep. 14, 2010 (6 pages).
International Search Report, from PCT/US10/36829, mailed Sep. 9, 2010 (5 pages).
European Search Report, EP 10250732, dated Jul. 28, 2010.

International Search Report and Written Opinion for Application No. PCT/US2010/037190, dated Sep. 22, 2010 (15 pages).
International Search Report and Written Opinion for Application No. PCT/US2010/036806, dated Sep. 3, 2010 (8 pages).
International Search Report and Written Opinion for Application No. PCT/US2010/036820, dated Oct. 22, 2010 (18 pages).

* cited by examiner

METHODS AND DEVICES FOR PROVIDING ACCESS THROUGH TISSUE TO A SURGICAL SITE

FIELD OF THE INVENTION

The present invention relates to methods and devices for providing access through tissue to a surgical site.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become more common as they provide minimally invasive techniques for establishing a portal for a number of procedures, such as those involving the abdominal cavity. Reduced postoperative recovery time, markedly decreased post-operative pain and wound infection, and improved cosmetic outcome are well established benefits of minimally invasive surgery, derived mainly from the ability of surgeons to perform an operation utilizing smaller incisions of the body cavity wall.

In many surgical procedures, it is desirable to provide one or more working channels into a body cavity through which various instruments can be passed to view, engage, and/or treat tissue to achieve a diagnostic or therapeutic effect. In laparoscopic abdominal procedures for example, the abdominal cavity is generally insufflated with $CO_2$ gas to a pressure of around 15 mm Hg. The abdominal wall is pierced and one or more tubular cannulas, each defining a working channel, are inserted into the abdominal cavity. A laparoscopic telescope connected to an operating room monitor can be used to visualize the operative field and can be placed through one of the working channels. Other laparoscopic instruments such as graspers, dissectors, scissors, retractors, etc. can also be placed through one or more of the working channels to facilitate various manipulations by the surgeon and/or surgical assistant(s).

While effective, there can be disadvantages when using a typical access port. For example, the access port could extend a distance above and/or a distance below the tissue in which it is positioned, which can interfere with access to the surgical field. For another example, tissue thicknesses and natural or artificial openings in which access ports are positioned can vary, and a typical access port can have a size too large or too small for secure positioning within a patient's tissue. Moreover, it can be difficult and time-consuming during the stress of surgery to choose a properly sized access port, particularly in a single surgical procedure using multiple access ports positioned in differently sized tissue openings and/or if surgical instruments of different sizes will be inserted through the access port.

Accordingly, there remains a need for methods and devices for providing access through tissue to a surgical site.

SUMMARY OF THE INVENTION

The present invention generally provides methods and devices for providing access through tissue to a surgical site. In one embodiment, a surgical device is provided that includes a sealing element formed of a puncturable self-sealing material having a durometer of at least about 5 Shore A and having formed therein a plurality of pores such that the pore volume in the sealing element is at least about 1%.

The sealing element can have any size, shape, and configuration, and can be formed of any one or more materials. The sealing element can be configured to form a channel seal when no surgical instrument is disposed therethrough and configured to form an instrument seal around a surgical instrument inserted therethrough. In some embodiments, the self-sealing material of the sealing element can have a durometer in a range of about 5 to 20 Shore A. The volume of the pores in the sealing element can be in a range of about 40% to 80%. At least some of the pores can be linked to one another and/or the pores can be independent of one another. The pores can each have a size in a range of about 5 to 50 μm. In some embodiments, the sealing element can have a tubular shape with a cannulated interior having a gel disposed in the cannulated interior. The gel can be configured to have a surgical instrument inserted therethrough from outside a body and into a body cavity and form a seal around the surgical instrument.

The sealing element can optionally include at least one layer of a gel material covering at least one face of the puncturable self-sealing material. The gel material can be formed of any one or more materials, such as a material having a durometer of less than about 5 Shore A. In some embodiments, the gel material can include a plurality of discrete voids formed therein. The voids can have any arrangement in the gel material, such as arranged around a perimeter of the sealing element.

The device can vary in any other number of ways. For example, the device can include a housing configured to be positioned proximal to an outer surface of tissue, with the sealing element being seated in the housing. A retractor can be configured to attach to the housing, can be configured to be positioned within an opening in tissue, and can have a working channel extending therethrough for forming a pathway through tissue into a body cavity. For another example, the device can include a retractor configured to be positioned within an opening in tissue, with the sealing element being seated in a working channel of the retractor.

In another embodiment, a surgical device includes a sealing element configured to have a surgical instrument inserted therethrough from outside a body into a body cavity. The sealing element can be formed of a puncturable self-sealing material having at least one discrete pocket contained therein. The device can vary in any number of ways. For example, the puncturable self-sealing material can have a plurality of discrete pockets formed therein. For another example, the puncturable self-sealing material can have a durometer greater than about 5 Shore A, have a durometer less than about 5 Shore A, or include a combination thereof. In some embodiments, the puncturable self-sealing material can be formed of a material having a durometer greater than about 5 Shore A that has a plurality of discrete pockets formed therein such that the puncturable self-sealing material has a durometer less than about 5 Shore A.

In another aspect, a surgical method is provided that includes positioning a surgical access device having a puncturable sealing element within an opening in tissue in a body of a patient, inserting a surgical instrument through the sealing element and into a body cavity underlying the tissue, and moving at least a shaft of the surgical instrument relative to the sealing element in a direction that is not parallel to a longitudinal axis of the shaft. The sealing element can dynamically form a seal around the surgical instrument and can maintain a seal around the surgical instrument when at least the shaft of the surgical instrument moves. The method can vary in any number of ways. In some embodiments, moving at least the shaft of the surgical instrument relative to the sealing element can cause at least one discrete void formed in the sealing element to distort in shape.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
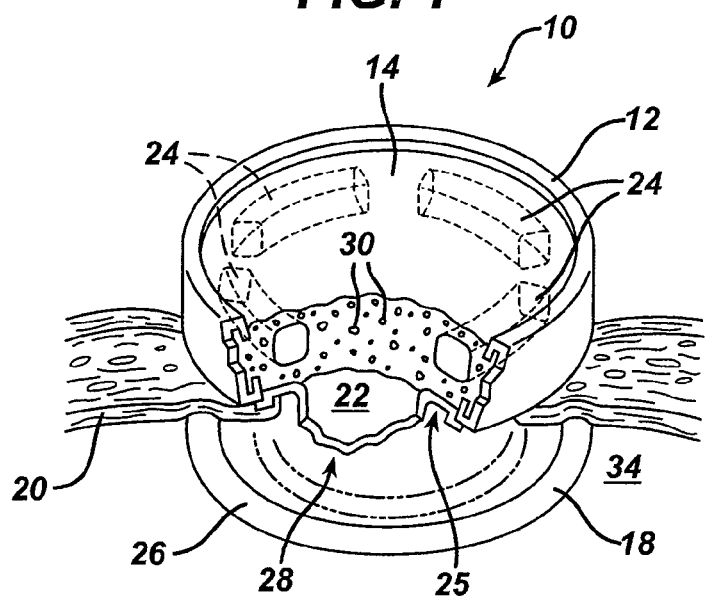
FIG. 1 is a partial cross-sectional perspective view of one embodiment of a surgical access device positioned in tissue and having a foam sealing element.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for providing access through tissue to a surgical site. Generally, a surgical access device can be configured to be positioned in tissue to provide access through a working channel of the access device to a body cavity underlying the tissue. The access device can include a sealing element positioned at least partially within the working channel. The sealing element can be formed of a puncturable self-sealing material configured to provide a channel or zero-closure seal that seals the working channel when no instrument is inserted through the sealing element and configured to provide an instrument seal that provides a seal around one or more surgical instruments inserted through the sealing element. When a surgical instrument inserted through the sealing element moves relative to the sealing element, the sealing element can be configured to maintain a complete seal around the instrument, thereby helping to prevent insufflation gas from escaping the body cavity through the access device and to prevent introduction of unwanted foreign material into the body cavity through the access device.

The various surgical access devices described herein can generally be configured to allow one or more surgical instruments to be inserted therethrough through a sealing element of the access device and into a body cavity. In one embodiment, a surgical access device can include the sealing element being seated in a proximal housing, hereinafter generally referred to as a housing, and a distal retractor. The distal retractor, hereinafter generally referred to as a retractor, can be configured as a wound protector, or other member for forming a pathway through tissue. The retractor can extend from the proximal housing of the device, and it can be configured to be positioned within an opening in a patient's body, such as the umbilicus. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

Any and all embodiments of a surgical access device can also include one or more safety shields positioned through, in, and around any of the components and/or tissue to protect the components against puncture or tear by surgical instruments being inserted through the device. Exemplary embodiments of safety shields are described in more detail in U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, which are hereby incorporated by reference in their entireties.

In any and all of the surgical access device embodiments disclosed herein, an engagement and/or release mechanism can be included to allow certain components of the surgical access device to be removable as needed, such as removable coupling of a housing and a retractor. Any engagement and release mechanism known in the art, e.g., a snap-lock mechanism, corresponding threads, etc., can be used to releasably mate components of the device. Exemplary embodiments of an engagement and release mechanisms are described in more detail in previously mentioned U.S. patent application Ser. No. 12/242,765 entitled "Surgical Access Device" filed on Sep. 30, 2008, U.S. patent application Ser. No. 12/399,625 entitled "Methods and Devices for Providing Access to a Body Cavity" filed on Mar. 6, 2009, and U.S. patent application Ser. No. 12/399,482 entitled "Methods and Devices for Providing Access to a Body Cavity" filed on Mar. 6, 2009 and in U.S. Pat. No. 7,371,227 entitled "Trocar Seal Assembly," issued May 13, 2008 and U.S. Pat. No. 5,628,732 entitled "Trocar With Improved Universal Seal," issued May 13, 2007, which are hereby incorporated by reference in their entireties.

In use, as further discussed below, the surgical access devices disclosed herein can be used to provide access to a patient's body cavity through a working channel of the access device that can extend at least through the retractor. The device's retractor can be positionable within an opening in a patient's body such that a distal portion of the retractor extends into a patient's body cavity and a proximal portion configured to couple to the device's housing is positioned adjacent to the patient's skin on an exterior of the patient's body. A lumen in the retractor can form a pathway through the opening in a patient's body so that surgical instruments can be inserted from outside the body to an interior body cavity. The elasticity of the skin of the patient can assist in the retention of the retractor in the body opening or incision made in the body. The retractor can be placed in any opening within a patient's body, whether a natural orifice or an opening made by an incision. As a non-limiting example, the retractor can be placed through the umbilicus. In one embodiment, the retractor can be substantially flexible so that it can easily be maneuvered into and within tissue as needed. In other embodiments, the retractor can be substantially rigid or substantially semi-rigid. The retractor can be formed of any suitable material known in the art, e.g., silicone, urethane, thermoplastic elastomer, and rubber. In one exemplary embodiment, as discussed further below, the retractor can be formed of a foam material configured to move between a compressed configuration and an expanded configuration to dynamically adjust to a size and shape of an opening in a patient's body.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough.

The surgical access devices disclosed herein can each include at least one sealing element configured as a seal to provide an instrument seal that forms a seal around an instrument disposed therethrough, but otherwise does not form a seal when no instrument is disposed therethrough; at least one channel seal or zero-closure seal that seals the working channel of the device when no instrument is disposed therethrough; or a combination instrument seal and channel seal that is effective to both form a seal around an instrument disposed therethrough and to form a seal in the working channel of the device when no instrument is disposed therethrough. In an exemplary embodiment, as discussed further below, the sealing element can be configured to provide both a channel seal and an instrument seal and to maintain the instrument seal around a surgical instrument when the instrument moves relative to the sealing element during the course of a surgical procedure. A person skilled in the art will appreciate that any one or more various seals known in the art can be used in combination with the sealing elements disclosed herein, including, e.g., duckbill seals, cone seals, flapper valves, diaphragm seals, lip seals, iris seals, etc. Exemplary embodiments of various seal protectors are described in more detail in U.S. Pat. No. 5,342,315 entitled "Trocar Seal/Protector Assemblies," issued Aug. 30, 1994 and U.S. Pat. No. 7,163,525 entitled "Duckbill Seal Protector," issued Jan. 16, 2007, which are hereby incorporated by reference in their entireties.

The sealing element can be formed of any one or more materials in any combination. Generally, the material can include a composite material, e.g., a gel or gel-like material or a foam or foam-like material, through which at least one surgical instrument can be inserted from outside a patient's body into a body cavity. The composite material can have micro-mechanical properties that differ from its macro-mechanical properties, which can allow differently sized surgical instruments to be sequentially and/or simultaneously inserted therethrough while providing reduced wear, reduced friction, and better durability than a material having micro-mechanical and macro-mechanical properties that are the same. In an exemplary embodiment, the sealing element can include one or more fluid pockets configured to help ease movement of a surgical instrument inserted through the sealing element and/or maintain an instrument seal around a surgical instrument inserted through the sealing element. Generally, fluid pockets include enclosed volumes contained in sealing element material. As discussed further below, a sealing element can include fluid pockets in the form of larger voids, e.g., discrete volumes formed at particular locations in a material, or smaller pores, e.g., bubbles irregularly distributed within a material. The fluid pockets can have any size, e.g., about 5 to 15 mm for voids and about 0.01 to 0.5 mm for pores, and fluid pockets in a sealing element can have the same or different size from any other fluid pockets in the sealing element. Although the embodiments of sealing elements illustrated and discussed below include air pockets, a person skilled in the art will appreciate that any one or more fluids, e.g., gases and/or liquids, can be disposed in the fluid pockets, same or different from any other fluid disposed in fluid pockets in the same sealing element.

In one exemplary embodiment, the puncturable, self-sealing material can include a gel or gel-like material having a durometer of less than about 5 Shore A and/or having an elongation greater than about 1000%. While a person skilled in the art will appreciate that any gel material can be used, a non-limiting example of a gel material includes a combination of an internal low molecular weight chemical species such as mineral oil or other oil, plasticizer, etc. and Kraton™ Rubber, e.g., styrene-ethylene/butylene-styrene (S-E/B-S) tri-block polymer, available from Kraton Polymers LLC of Houston, Tex.

As mentioned above, the gel material can include one or more fluid pockets, which in the gel material can generally include one or more voids. The voids can be formed in the gel material in a variety of ways, as will be appreciated by a person skilled in the art. In one exemplary embodiment, one or more voids can be formed in a gel material by injecting a fluid, e.g., air, into the gel material as the gel material becomes tacky during the curing process. The fluid can be injected into the gel material in one or more discrete locations to form one or more discrete voids in a closed configuration such that the voids are isolated and independent of one another. A person skilled in the art will appreciate that discrete voids can be formed in the gel material in this or in any other way. The discrete locations can be anywhere in the gel material, but in an exemplary embodiment, the discrete locations can be around a perimeter of the gel material to help provide a void-free center portion through which a surgical instrument can be inserted with less chance of being inserted through a void. The voids can have any total volume in the gel material, e.g., in a range of about 40% to 80%. The greater the volume of voids in the gel material, the softer the macro-mechanical durometer of the gel material. The voids can have any shape, e.g., cubed, rectangular prism-shaped, spherical, wedge-shaped, etc., same or different from any one or more voids in the gel material.

In another exemplary embodiment, the puncturable, self-sealing material can include a foam or foam-like material having an elongation less than about 100% and/or having a durometer of greater than about 5 Shore A, e.g., 10 Shore A, in a range of about 5 Shore A to 20 or Shore A, and up to about 95 Shore A. Generally, a foam material can have a lower elastic modulus than a gel material, e.g., about 10% of the elastic modulus of a gel material. While a person skilled in the art will appreciate that any foam material can be used, non-limiting examples of a foam material includes Kraton™ Rubber, silicone elastomers, polyurethanes, polyolefins such as polypropylene and polyethylene, polyolefin elastomers such as Santoprene™, e.g., a crosslinked co-polymer of polypropylene and EPDM (ethylene propylene diene M-class) rubber, available from Advanced Elastomer Systems, LP of Akron, Ohio, polyethylene-co-vinyl acetate copolymers, polytetrafluoroethylene (PTFE) in the form of expanded PTFE, etc.

As mentioned above, the foam material can include one or more fluid pockets, which in the foam material can generally include one or more voids and/or one or more pores. The voids can be formed in the foam material in any way, as discussed above. The pores can be formed in the foam material in a variety of ways, as will be appreciated by a person skilled in the art. In an exemplary embodiment, one or more pores can be formed in a foam material in an open configuration such that at least some of the pores are linked to one another. Having pores in an open configuration, a foam material can have a lower macro-durometer than having pores solely in a closed configuration because at least some of the pores can be evacuated to allow the foam material to compress or collapse more completely under a mechanical load. Pores can be formed in an open configuration in a variety of ways, as will be appreciated by a person skilled in the art, such as by whipping air bubbles into the foam-material before it completely sets. The pores can have any size, e.g., in a range of about 1 to 500 μm or in a range of about 5 to 50 μm. The greater the volume of pores in the foam material, the softer the macro-mechanical durometer of the foam material. The pores can also have any shape, e.g., cubed, rectangular prism-shaped, spherical, wedge-shaped, etc., same or different from any one or more pores in the foam material. A person skilled in the art will appreciate that a foam material can include voids in a closed configuration, pores in a closed configuration, and/or pores in an open configuration. The pores and/or voids can have any total volume in the foam material, e.g., in a range of about 40% to 80%.

A surgical access device can include a sealing element formed of a gel material and/or a foam material. In an exemplary embodiment, shown in FIGS. 1 and 2, a surgical access device 10 is provided having a housing 12 configured to have one or more surgical instruments inserted therethrough. Although the housing 12 can have any configuration, in this illustrated embodiment, the housing 12 includes a sealing element 14 seated therein that is configured to form a seat and seal between the sealing element 14 and a distal portion of the device 10, e.g., a retractor 18. The housing 12 can be fixedly or removably coupled to the retractor 18 configured to distally extend from the housing 12 and configured to provide a pathway through tissue into a body cavity. In some embodiments, the sealing element can be seated in the retractor, with or without a housing removably or fixedly attached to the retractor. The retractor can optionally include a distal retractor portion coupled to a proximal retractor portion or proximal retractor base, with the housing and/or the sealing element being configured to be seated in the proximal retractor portion or proximal retractor base.

As noted above, the retractor 18 can extend distally from the housing 12, and it can be configured to be positioned in an opening 16 formed in tissue 20 and to define a working channel 22 extending therethrough. The retractor 18 can, as shown in this exemplary embodiment, include a substantially flexible distal portion 22 having a proximal flange 25 and a distal flange 26 with an inner elongate portion 28 extending therebetween. The inner elongate portion 28 can have a diameter less than a diameter of the proximal flange 25 and the distal flange 26, which can have the same diameter or different diameters from one another, and can be configured to be positioned within the tissue 20. A distal o-ring (not shown) can optionally be positioned within the distal flange 26 to provide structural support to the retractor 18 within a patient's body. The distal o-ring can be substantially flexible or substantially rigid as needed for use in a particular application. In some embodiments, the retractor can additionally or alternatively include a proximal o-ring.

As shown in this embodiment, the housing 12 can be removably coupled via snap-fit to the retractor 18, which as illustrated in this embodiment can be flexible. The housing 12 can be in a fixed position relative to the retractor 18 as shown in this embodiment, or the housing 12 can be movable relative to the retractor 18. Exemplary embodiments of various housings are described in more detail in previously mentioned U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, and in U.S. patent application Ser. No. 12/399,547 entitled "Surgical Access Devices And Methods Providing Seal Movement In Predefined Paths" filed on Mar. 6, 2009 and U.S. patent application Ser. No. 12/427,964 entitled "Methods And Devices For Identifying Sealing Port Size" filed on Apr. 22, 2009, which are hereby incorporated by reference in their entireties.

Figure 3:
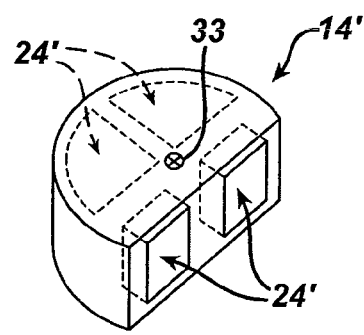
FIG. 3 is a cross-sectional perspective view of one embodiment of a foam sealing element having a plurality of voids contained therein.

While the device 10 can include a sealing element having any size, shape, and configuration, as in this illustrated embodiment the sealing element 14 can have a substantially cylindrical shape and be formed of a foam material. Although the sealing element 14 is shown as having a substantially planar proximal surface, the sealing element 14 can be concave or convex, e.g., domed, to permit a third dimension of movement. As mentioned above, the sealing element 14 can include at least one fluid pocket in the form of a void 24 and a plurality of fluid pockets in the form of pores 30. Although the sealing element 14 includes four rectangular prism-shaped voids 24 arranged equidistantly around a perimeter of the sealing element 14, the sealing element 14 can include any number of voids having any shape, size, and position within the sealing element. For non-limiting example, FIG. 3 illustrates another embodiment of a sealing element 14' including a plurality of pie-shaped or wedge-shaped voids 24' contained therein and arranged around a perimeter of the sealing element 14'.

Figure 2:
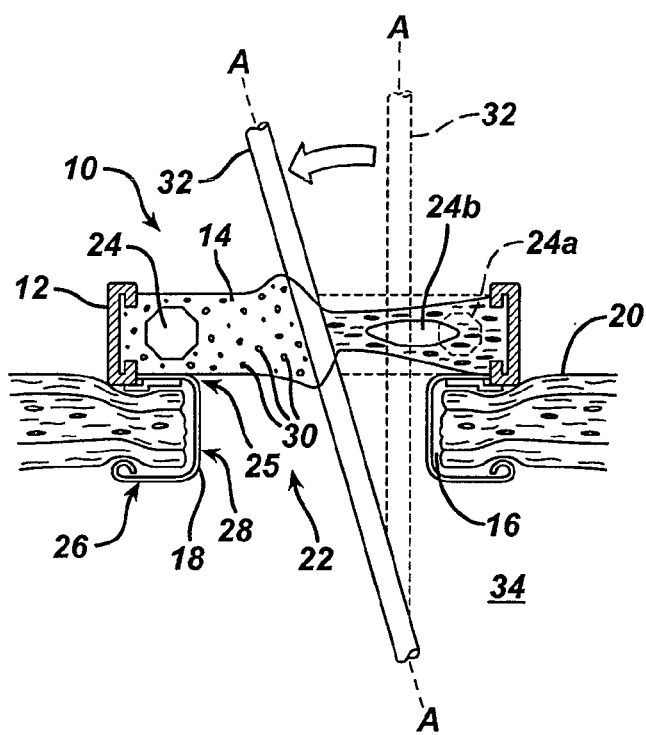
FIG. 2 is a side cross-sectional view of the device of FIG. 1 with a surgical instrument inserted therethrough.

In use, as shown in FIG. 2, the retractor 18 can be positioned within the opening 16 in the tissue 20, before or after the housing 12 is attached thereto. A surgical instrument 32 can be inserted through the sealing element 14 at a first position relative to the sealing element 14, as shown by the surgical instrument 32 drawn in phantom in FIG. 2. The surgical instrument 32 can have any size, e.g., 10 mm, 12 mm, 7 mm, 3 mm, 5 mm, 25 mm, etc., and include any type of surgical device such as a grasper, a scoping device (e.g., an endoscope, a laparoscope, and a colonoscope), a cutting instrument, etc. A person skilled in the art will appreciate that the term "grasper" as used herein is intended to encompass any surgical instrument that is configured to grab and/or attach to tissue and thereby manipulate the tissue, e.g., forceps, retractors, movable jaws, magnets, adhesives, stay sutures, etc. A person skilled in the art will also appreciate that the term "cutting instrument" as used herein is intended to encompass any surgical instrument that is configured to cut tissue, e.g., a scalpel, a harmonic scalpel, a blunt dissector, a cautery tool configured to cut tissue, scissors, an endoscopic linear cutter, a surgical stapler, etc. The first position can be at a location such that the surgical instrument 32 does not contact any of the voids 24, as shown, although the first position of the surgical instrument 32 can be anywhere with respect to the sealing element 14. The sealing element 14 can be formed of a material that is at least partially transparent, which can allow the locations of the voids 24 to be visually identified to help the surgical instrument 32 be inserted through the sealing element 14 without intersecting any of the voids 24. Alternatively or in addition, the sealing element 14 can include one or more markers (not shown) to indicate locations of the voids 24, e.g., a line drawn, scored, or otherwise identifiable on a proximal surface of the sealing element 14 indicating an interior region of the sealing element 14 that does not contain any voids 24, at least one marking 33 (FIG. 3) in the form of an "x" or other symbol, character, etc. positioned at a target insertion location on a proximal surface of the sealing element 14', etc. Whether or not the instrument 32 inserted through the sealing element 32 passes through any of the voids 24, the sealing element 14 can self-seal around the surgical instrument 32.

The surgical instrument 32 can be moved from the first position to a second, different position relative to the sealing element 14, as shown by the surgical instrument drawn in solid lines in FIG. 2. In other words, at least a shaft of the surgical instrument 32 (only the shaft of the instrument 32 is illustrated in FIG. 2) can be moved relative to the sealing element 12 in a direction that is not parallel to a longitudinal axis A of the shaft, e.g., laterally moved to a different position within the perimeter of the sealing element 14 relative to a center point of the sealing element 14. When the instrument 32 moves from the first position to the second position, the foam material of the sealing element 14 can move or "bunch" with one or more of the voids 24 distorting in shape while maintaining its volume as an air pocket contained within the sealing element 14, e.g., deforming from a resting, default void configuration 24a with the instrument 32 in the first position to a distorted or deformed void configuration 24b with the instrument 32 in the second position. One or more of the pores 30 can also similarly distort or deform when the instrument 32 moves from the first position to the second position. Having the pores 30 and/or the voids 24 can thus provide the surgical instrument 32 with freedom of movement and allow the sealing element 14 to "bunch" while maintaining a seal around the surgical instrument 32 when at least the shaft of the surgical instrument 32 moves relative to the sealing element 14, e.g., without providing any open space between the instrument 32 and the sealing element 14 through which fluid or other material can enter or escape. A person skilled in the art will appreciate that the surgical instrument 32 can alternatively or additionally be pivotally and/or longitudinally moved in the first position and/or in the second position, e.g., by tilting the surgical instrument 32 or by moving the shaft of the surgical instrument 32 up and/or down parallel to its longitudinal axis A. A person skilled in the art will also appreciate that although only one instrument 32 is shown inserted through the sealing element 14 into a body cavity 34 underlying the tissue 20, any number of surgical instruments can be simultaneously or sequentially inserted through the sealing element 14.

Figure 4:
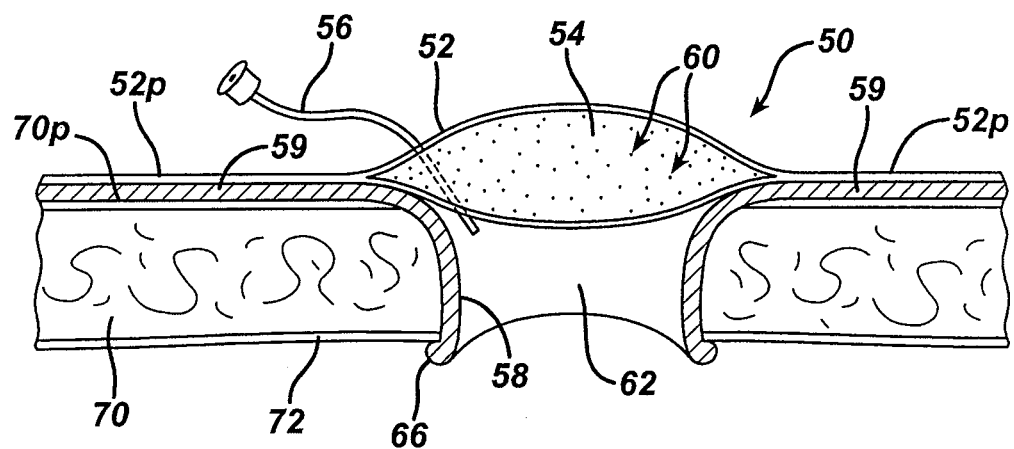
FIG. 4 is a side cross-sectional view of one embodiment of a surgical access device positioned in tissue and having a buttress and a foam sealing element.

In some embodiments, the sealing element can include a buttress or protective layer to help protect the sealing element and attach the device in a secure position relative to tissue in which the device is positioned. FIG. 4 illustrates an exemplary embodiment of a surgical access device 50 that includes a housing, buttress, or protective layer 52, a sealing element 54 configured to be seated in the housing 52, and a retractor 58 configured to releasably or fixedly couple to the housing 52. The retractor 58, as well as other embodiments of retractors described herein, can be configured and used similar to the retractor 58 discussed above. The housing 52 can generally be configured and used similar to the housing 52 discussed above, as can other embodiments of housings described herein, but in this embodiment, the housing 52 can be configured as buttress or protective layer configured to enclose the sealing element 54. The sealing element 54 as shown includes a foam material having a plurality of pores 60 contained therein, but the sealing element 54 can include a foam material and/or a gel material with or without voids and/or pores. The device 50 also includes an insufflation port 56 extending through the housing 52 and through the sealing element 54 into a working channel 62 of the retractor 58.

The housing 52 can have any size, shape, and configuration, and can be formed of any material. As shown in this illustrated embodiment, the housing 52 can be formed of a foam material having a cavity formed therein in which the sealing element 54 can be disposed. The housing 52 can include a proximal flange 52p extending radially outward. The retractor 118 can include a corresponding proximal flange 59 radially extending outward that is configured to releasably or fixedly couple with the housing's proximal flange 52p and to be positioned adjacent to and/or against an outer or proximal surface 70p of tissue 70 in which the device 50 can be positioned. In some embodiments, the housing's proximal flange 52p can be configured to engage the proximal surface 70p of the tissue 70. A diameter of the retractor's proximal flange 59 can be equal to or greater than a diameter of the housing's proximal flange 52p. One or both of the housing 52 and the retractor 58, e.g., the proximal flanges 59, 52p, can optionally include an attachment mechanism (not shown) such as a textured gripping surface, adhesive (with or without a removable, protective backing), corresponding protrusions and depressions, etc., to help couple the housing 52 and the retractor 58. Additionally or alternatively, a distal, tissue-contacting surface of the retractor's proximal flange 59 and/or a proximal, tissue-contacting surface of the retractor's distal flange 66 can include an attachment mechanism (not shown) to help secure the retractor 58 in position relative to the tissue 70, e.g., by attaching to fascia 72.

Figure 5:
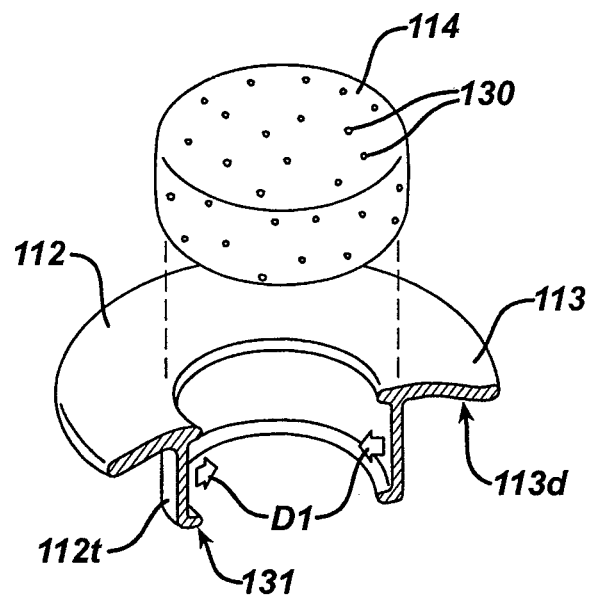
FIG. 5 is a partial cross-sectional perspective view of one embodiment of a housing and a foam sealing element.
Figure 6:
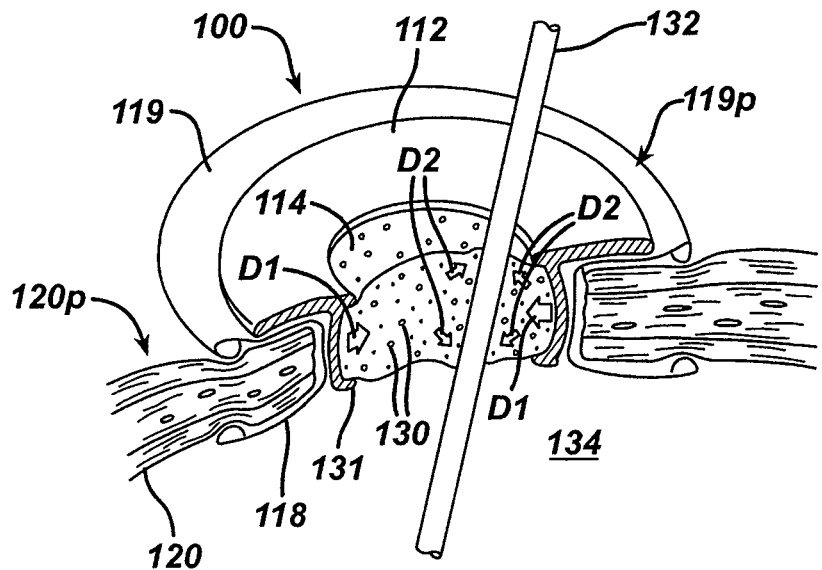
FIG. 6 is a cross-sectional perspective view of one embodiment of a surgical access device including the housing and the sealing element of FIG. 5 with the device positioned in tissue and having a surgical instrument inserted through the device.
Figure 7:
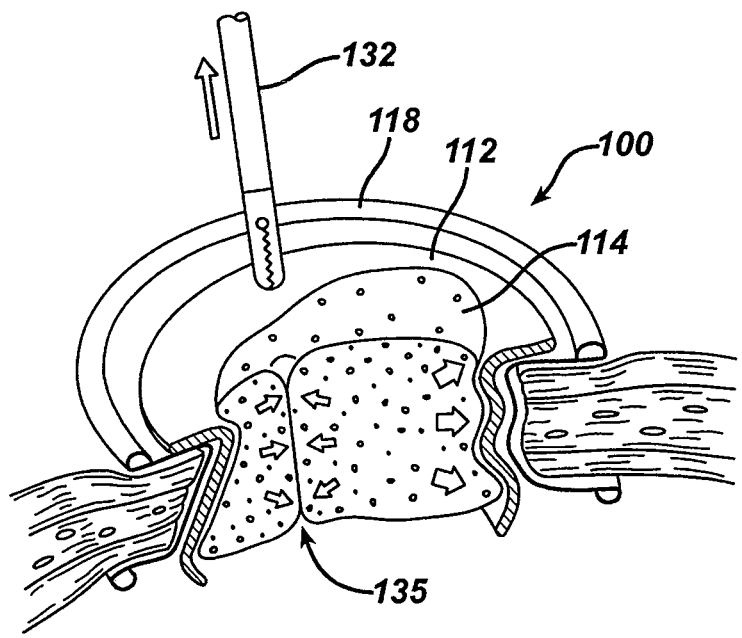
FIG. 7 is a cross-sectional perspective view of the surgical access device of FIG. 6 with the surgical instrument being removed from the device.

FIGS. 5-7 illustrate another embodiment of a surgical access device 100 that includes a housing 112, a sealing element 114 configured to be seated in the housing 112, and a retractor 118 configured to releasably or fixedly couple to the housing 112. In this embodiment, the housing 112 can be configured as an elastomeric sleeve including an elongate tubular portion 112*t* configured to extend into a working channel 122 of the retractor 118. The retractor 118 can include a proximal flange 119 radially extending outward that is configured to be positioned adjacent to and/or against an outer or proximal surface 120*p* of tissue 120 in which the retractor 118 can be positioned. The housing 112 can include a corresponding, radially extending proximal flange 113 configured to couple with the retractor's proximal flange 119, e.g., with a distal surface 113*d* of the housing's proximal flange 113 engaging a proximal surface 119*p* of the retractor's proximal flange 119. In some embodiments, the housing's proximal flange 113 can be configured to engage the proximal surface 120*p* of the tissue 120. A diameter of the retractor's proximal flange 119 can be greater than a diameter of the housing's proximal flange 113, as illustrated in this embodiment. One or both of the housing 112 and the retractor 118, e.g., the proximal flanges, an interior surface of the retractor's working channel, etc., can optionally include an attachment mechanism (not shown) such as a textured gripping surface, adhesive (with or without a removable, protective backing), corresponding protrusions and depressions, etc., to help couple the housing 112 and the retractor 118. Additionally or alternatively, a distal, tissue-contacting surface of the retractor's proximal flange 119 and/or a proximal, tissue-contacting surface of the retractor's distal flange can include an attachment mechanism (not shown) to help secure the retractor 118 in position relative to the tissue 120.

As illustrated, the sealing element 114 can be configured to be seated in the housing 112, e.g., in the elongate tubular portion 112*t* of the housing 112. The elongate tubular portion 112*t* can be biased inwards, as indicated by directional arrows D1, which can help retain the sealing element 114 therein. The elongate tubular portion 112*t* can optionally include a distal flange 131 extending radially inward that is configured to help seat the sealing element 114 and prevent it from distally sliding out of the housing 112. Similarly, the housing's proximal flange 113 can optionally extend radially inward to help secure the sealing element 114 to the housing 112 and prevent it from proximally sliding out of the housing 112. The sealing element 114 can be compressible or collapsible to help pass the sealing element 114 over one of the flanges 113, 119 and into the elongate tubular portion 112*t*. The sealing element 114 can be formed of any material and include any number and type of fluid pockets as discussed above, but in this embodiment, the sealing element 114 includes a foam cylindrical member having a plurality of pores 130 formed therein.

As shown in FIG. 6, the device 100 can be used similar to the device 10 discussed above. The retractor 118 can be positioned within an opening 116 in the tissue 120, before or after the housing 112 is attached thereto. The sealing element 114 can be coupled to the housing 112 before or after the housing 112 is attached to the retractor 118. A surgical instrument 132 can be inserted through the sealing element 114 to access a body cavity 134 underlying the tissue 120. The sealing material 114 can exert a force toward the surgical instrument 132, as indicated by directional arrows D2 in FIG. 6, which along with the inwardly directed force exerted by the housing 112 shown by the arrows D1, can help form a seal around the instrument 132 that can be maintained when the instrument 132 moves relative to the sealing element 114. When the instrument 132, shown in this embodiment in FIG. 7 as a grasper having a pair of movable jaws at a distal end of an elongate shaft, is removed from the device 100, the sealing element 114 can maintain a channel seal by self sealing a channel 135 formed when the instrument 132 was inserted through the sealing element 114.

Figure 8:
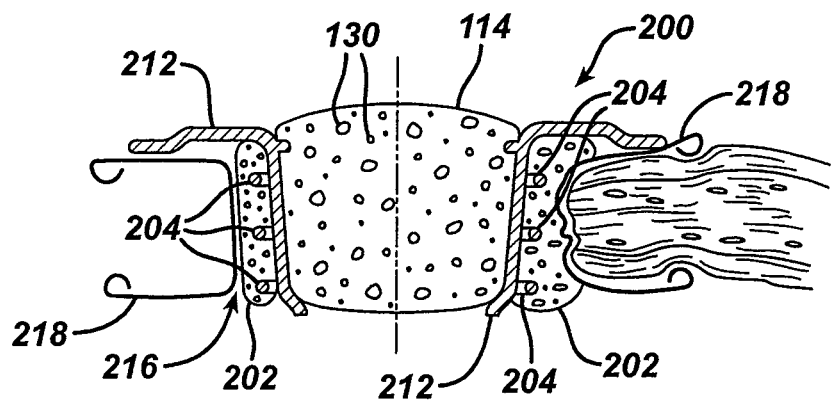
FIG. 8 is a side cross-sectional view of one embodiment of a surgical access device positioned in tissue and including a foam sealing element and an expandable member.

FIG. 8 illustrates another embodiment of a surgical access device 200 including a retractor 218, a housing 212, and a sealing element 214 formed of a foam material and including a plurality of pores 230. As shown in this embodiment, the housing 212 can have a deformable expandable member 202 coupled thereto. Although any attachment mechanism can be used, in this embodiment, the housing 212 includes a plurality of connector prongs 204 configured to pierce and hold the expandable member 202. The expandable member 202 can generally be configured to engage an inner surface of the retractor 218, e.g., an inner surface of the retractor's working channel, to help hold the housing 212 therein, to dynamically adjust to a size of a tissue opening 216 in which the device 200 is positioned, and to help provide a seal between the housing 212 and the retractor 218.

As mentioned above, a surgical access device can include a seal element formed of two or more layers of at least one gel material and at least one foam material. Optionally, an attachment mechanism such as an adhesive can be positioned between any of the layers to help secure the layers together. A multi-layer sealing element can allow for a lower weight sealing element than a sealing element formed entirely of a gel material, which can make a multi-layer sealing element easier to manipulate during surgery and to insert surgical instruments therethrough and move with respect thereto.

Figure 9:
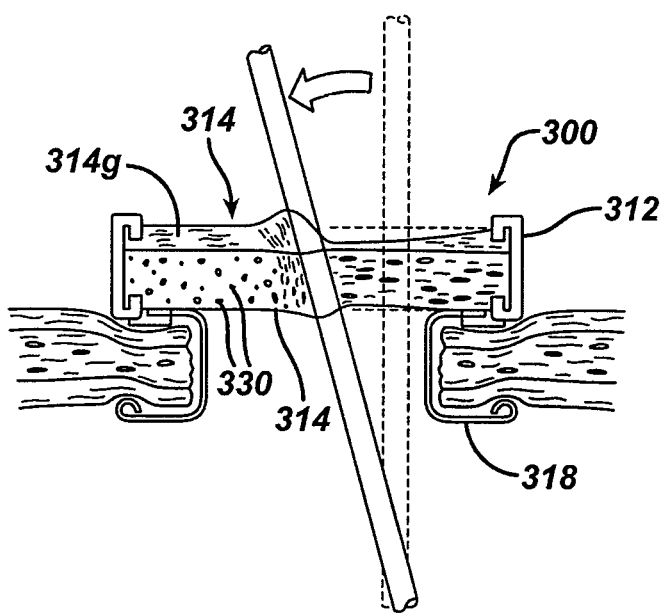
FIG. 9 is a side cross-sectional view of one embodiment of a surgical access device positioned in tissue and including a multi-layer sealing element, with a surgical instrument inserted through the device.

FIG. 9 illustrates one embodiment of a surgical access device 300 that includes a retractor 318, a housing 312, and a sealing element 314 having a gel proximal layer 314*g* and a foam distal layer 314*f* underlying the gel layer 314*g*. The gel and foam layers 314*g*, 314*f* can have any size, but in an exemplary embodiment, as illustrated, the gel and foam layers 314*g*, 314*f* can have substantially equal surface areas on their respective contact surfaces such that a face of the gel layer 314 can cover an opposing face of the foam layer 314*f*.

Figure 10:
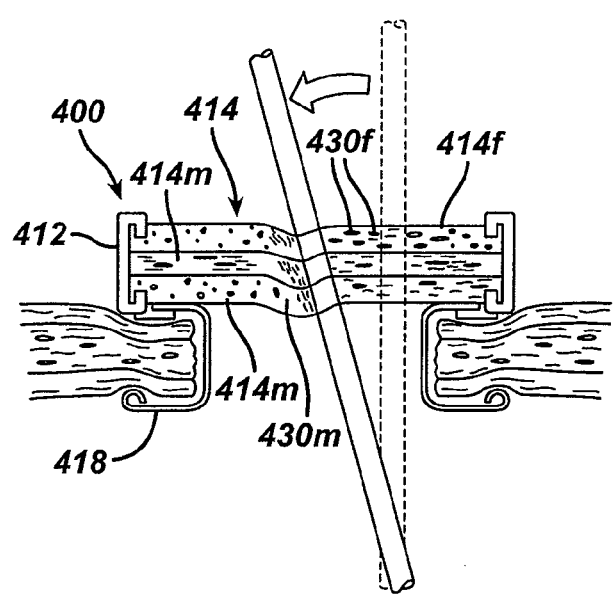
FIG. 10 is a side cross-sectional view of another embodiment of a surgical access device positioned in tissue and including a multi-layer sealing element, with a surgical instrument inserted through the device.

FIG. 10 illustrates another embodiment of a surgical access device 400 including a multi-layer sealing element 414, a retractor 418, and a housing 412. In this illustrated embodiment, the device 400 includes the sealing element 414 having first and second foam layers 414*f*, 414*m* and a gel layer 414*g* sandwiched between the foam layers 414*f*, 414*m*. The foam layers 3 14*f*, 414*f*, 414*m* of FIGS. 9 and 10 can respectively include a plurality of pores 330, 430*f*, 430*m*, as illustrated, and although not shown in these embodiments, as mentioned above the foam layers 314*f*, 414*f*, 414*m* and/or the gel layers 314*g*, 414*g* can include one or more fluid pockets in the form of voids.

Figure 11:
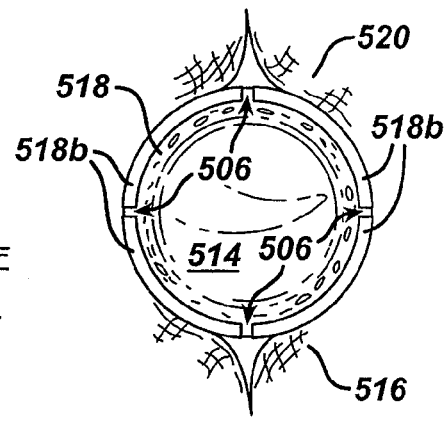
FIG. 11 is a top view of one embodiment of a surgical access device positioned in tissue and including a foam retractor and a gel sealing element.
Figure 12:
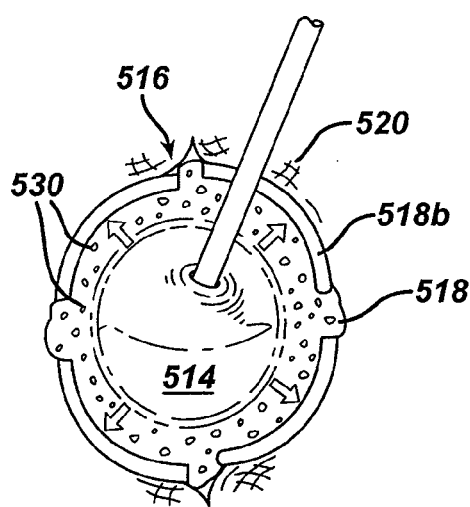
FIG. 12 is a top view of the device of FIG. 11 with a surgical instrument inserted through the device.
Figure 13:
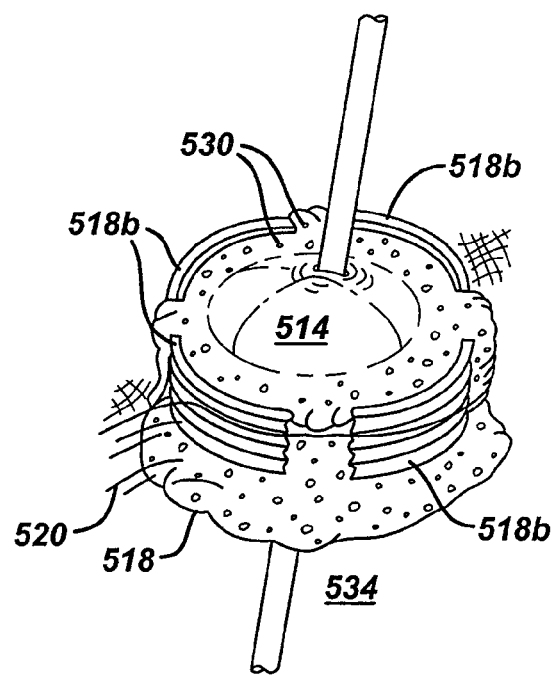
FIG. 13 is a perspective view of the device and the surgical instrument of FIG. 12.

In some embodiments, a retractor of a surgical access device can be formed of a foam material while a sealing element of the device can include a gel material disposed in a working channel of the retractor. In this way, an inward force exerted by the tissue in the tissue opening can compress the retractor to create a seal between the tissue and the retractor, while the retractor can exert an outward force. In this way, when positioned within an opening in tissue, the retractor can dynamically mold to a size and shape of the opening. FIGS. 11-13 illustrate one embodiment of a surgical access device 500 that includes a retractor 518 formed of a foam material and having a plurality of pores 530. The retractor 518 can also serve as housing by seating a sealing element 514 formed of a gel material in a working channel of the retractor 518. The device 500 can optionally include a proximal retractor base 518b configured to help grip a tissue opening 416 in which the device 500 can be positioned to help prevent longitudinal and/or rotational movement of the device 500 therein when the device 500 is positioned therein. The proximal retractor base 518b can include a continuous, expandable ring, or as shown, the proximal retractor base 518b can include a plurality of rims having spaces 506 located therebetween. The spaces 506 can be configured to allow the retractor 518 to expand when positioned in the tissue opening 516, as shown in FIGS. 12 and 13, to help enlarge the tissue opening 516 and to more tightly secure the device 500 therein. The retractor 518 can also be configured to expand in a distal portion thereof when positioned in the tissue opening 516, as shown in FIG. 13. In this way, the distal portion of the retractor 518 can expand against a distal surface of the tissue 520 in a body cavity 534 underlying the tissue 520 to act as a distal flange to help adjust the retractor 518 to a size and shape of the tissue opening 516 and better hold the retractor 518 therein.

Figure 14:
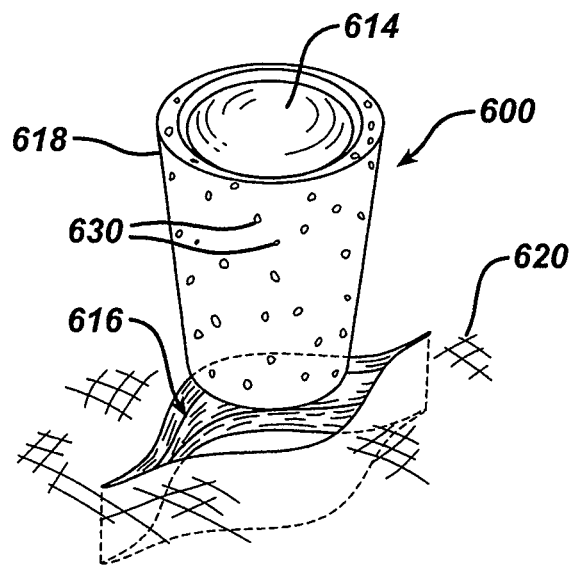
FIG. 14 is a perspective view of another embodiment of a surgical access device being positioned in tissue and including a foam retractor and a gel sealing element.
Figure 15:
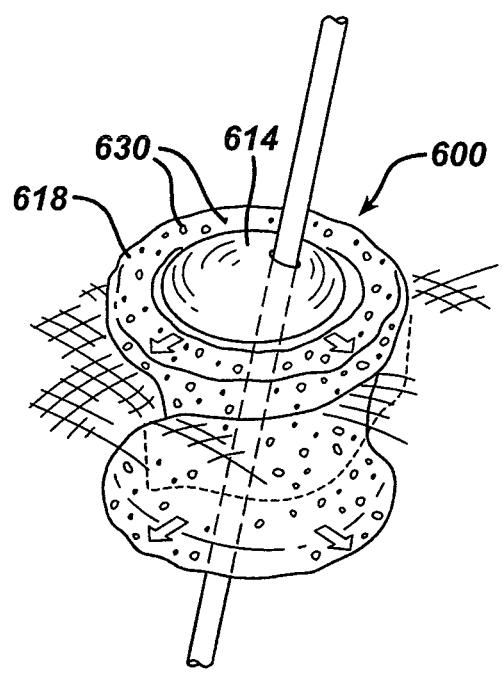
FIG. 15 is a perspective view of the device of FIG. 14 positioned in tissue and having a surgical instrument inserted therethrough.

FIGS. 14 and 15 illustrate another embodiment of a surgical access device 600 that includes a retractor 618 formed of a foam material and having a plurality of pores 630, with a sealing element 614 formed of a gel material disposed in a working channel of the retractor 618. Unlike the device 500 of FIGS. 11-13, the device 600 of FIGS. 14 and 15 does not include a proximal retractor base. Similar to a distal portion of the retractor 618 being configured to expand against a distal surface of tissue 620, a proximal portion of the retractor 618 can be configured to expand against a proximal surface of the tissue 620 to act as a proximal flange to help adjust the retractor 618 to a size and shape of a tissue opening 616 in which the device 600 can be positioned and more tightly secure the device 600 therein. Although the retractors 518, 618 of FIGS. 11-15 have a generally cylindrical shape with generally cylindrical working channels, the retractors 518, 618 and their working channels can have any shape.

In use, any of the surgical access devices described herein can be positioned within tissue as discussed above to provide access to a body cavity underlying the tissue. A surgical access device in use can be positioned within a tissue in a variety of ways. In one embodiment, the device can be positioned in tissue fully assembled in a default position, e.g., as shown in FIGS. 1 and 9. In another embodiment, the device can be positioned partially assembled in the tissue and be fully assembled with a portion of the device positioned in the tissue, e.g., a retractor of the device can first be positioned in the tissue and a housing of the device subsequently coupled to the retractor. If the tissue and/or the retractor are adequately flexible, the retractor can be angled or pivoted to a desired position to ease attachment of the housing to the retractor.

However positioned within the tissue, the device can be positioned within an opening or incision formed in the tissue, e.g., in the umbilicus. A proximal portion of the device can be positioned on and/or proximal to a proximal surface of the tissue, and a distal portion of the device can be positioned on and/or distal to a distal surface of the tissue in a body cavity underlying the tissue. A working channel or passageway of the device can thus extend through the tissue to provide a path of access to the body cavity.

With the surgical access device assembled and positioned in the tissue, one or more surgical instruments can be inserted therethrough and into the body cavity where the instruments can help perform any type of surgical procedure. The embodiments of surgical access devices illustrated and discussed below can be used in laparoscopic or other minimally invasive surgical procedures and/or in open surgical procedures in which any surgical instrument, including a hand, can be inserted through the surgical access device. One or more surgical instruments can be inserted through the device to help perform at least a portion of a surgical procedure. If the tissue and/or the retractor are adequately flexible, the retractor can be angled or pivoted during use of the device with the one or more surgical instruments inserted therethrough.

At any point before, during, or after a surgical procedure, if the device includes a housing it in full or part can be released from the retractor, and the retractor can be removed from the tissue. With the housing of the device disengaged from the retractor, the passageway of the retractor can still provide access to the body cavity underlying the tissue. One or more surgical instruments can be advanced through the passageway of the retractor, such as a waste removal bag configured to hold waste material, e.g., dissected tissue, excess fluid, etc., from the body cavity. The bag can be introduced into the body cavity through the retractor's passageway or other access port. A person skilled in the art will appreciate that one or more surgical instruments can be advanced through the retractor's passageway before and/or after the housing has been attached to the retractor.

As will be appreciated by those skilled in the art, any and all of the embodiments disclosed herein can be interchangeable with one another as needed. For example, an exemplary surgical access device kit could include multiple housings with one or more retractors, with each housing having different sealing elements. Various release mechanism known in the art can be used to releasably attach the various housings to a retractor.

There are various features that can optionally be included with any and all of the surgical access device embodiments disclosed herein. For example, a component of the device, such as a housing, retractor, etc., can have one or more lights formed thereon or around a circumference thereof to enable better visualization when inserted within a patient. As will be appreciated, any wavelength of light can be used for various applications, whether visible or invisible. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. application Ser. No. 12/242,333 entitled "Methods and Devices for Performing Gastrectomies and Gastroplasties" filed on Sep. 30, 2008; U.S. application Ser. No. 12/242,353 entitled "Methods and Devices for Performing Gastrectomies and Gastroplasties" filed on Sep. 30, 2008; and U.S. application Ser. No. 12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a housing, a proximal retractor base, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a sealing element formed of a puncturable self-sealing material having a durometer of at least about 5 Shore A, the sealing element having formed therein a plurality of pores such that the sealing element has a durometer of less than about 5 Shore A and a pore volume of at least about 1%; and
   a retractor configured to be positioned within an opening in tissue, the sealing element sealing in a working channel of the retractor.

2. The device of claim 1, wherein the sealing element is configured to form a channel seal when no surgical instrument is disposed therethrough and configured to form an instrument seal around a surgical instrument inserted therethrough.

3. The device of claim 1, wherein the self-sealing material has a durometer in a range of about 5 to 20 Shore A.

4. The device of claim 1, wherein the volume of the pores in the sealing element is in a range of about 40% to 80%.

5. The device of claim 1, wherein at least some of the pores are linked to one another.

6. The device of claim 1, wherein the pores are independent of one another.

7. The device of claim 6, wherein the pores each have a size in a range of about 5 to 50 μm.

8. The device of claim 1, wherein the sealing element includes at least one layer of a gel material covering at least one face of the puncturable self-sealing material.

9. The device of claim 8, wherein the gel material includes a plurality of discrete voids formed therein.

10. The device of claim 9, wherein the voids are arranged around a perimeter of the sealing element.

11. The device of claim 8, wherein the gel material is formed of a material having a durometer of less than about 5 Shore A.

12. The device of claim 1, further comprising a housing configured to be positioned proximal to an outer surface of tissue, the sealing element being seated in the housing.

13. The device of claim 1, wherein the sealing element has a tubular shape with a cannulated interior having a gel disposed in the cannulated interior, the gel configured to have a surgical instrument inserted therethrough from outside a body and into a body cavity and form a seal around the surgical instrument.

14. A surgical device, comprising:
   a sealing element configured to have a surgical instrument inserted therethrough from outside a body into a body cavity, the sealing element being formed of a puncturable self-sealing material which has a durometer of greater than about 5 Shore A and having at least one discrete pocket contained therein such that the sealing element has a durometer less than about 5 Shore A; and
   a retractor configured to be positioned within an opening in tissue, the sealing element being seated in a working channel of the retractor.

15. The device of claim 14, wherein the puncturable self-sealing material has a plurality of discrete pockets formed therein.

16. The device of claim 14, wherein the at least one discrete pocket has a size in a range of about 5 mm to 15 mm.

* * * * *